United States Patent
Mattison et al.

(10) Patent No.: US 12,325,674 B1
(45) Date of Patent: Jun. 10, 2025

(54) MODULAR SYSTEM FOR RENEWABLE FUEL GENERATION

(71) Applicant: General Galactic Technologies Corporation, El Segundo, CA (US)

(72) Inventors: Halen Garrett Mattison, Manhattan Beach, CA (US); Luke David Hall Neise, Los Angeles, CA (US); Anna Lee Tonkovich, Gilbert, AZ (US)

(73) Assignee: General Galactic Technologies Corporation, Los Angeles, CA (US)

( * ) Notice: Subject to any disclaimer, the term of this patent is extended or adjusted under 35 U.S.C. 154(b) by 0 days.

(21) Appl. No.: 18/607,293

(22) Filed: Mar. 15, 2024

(51) Int. Cl.
| | | |
|---|---|---|
| *B01J 8/04* | (2006.01) | |
| *B01J 8/06* | (2006.01) | |
| *C07C 1/12* | (2006.01) | |
| *C25B 1/04* | (2021.01) | |
| *C25B 15/08* | (2006.01) | |

(52) U.S. Cl.
CPC .................. *C07C 1/12* (2013.01); *B01J 8/04* (2013.01); *B01J 8/0496* (2013.01); *B01J 8/06* (2013.01); *B01J 8/067* (2013.01); *C25B 1/04* (2013.01); *C25B 15/081* (2021.01); *C25B 15/083* (2021.01); *B01J 2208/00132* (2013.01); *B01J 2208/00212* (2013.01); *B01J 2208/00513* (2013.01); *B01J 2208/0053* (2013.01); *B01J 2219/0002* (2013.01); *Y02C 20/40* (2020.08); *Y02E 60/36* (2013.01)

(58) Field of Classification Search
None
See application file for complete search history.

(56) References Cited

U.S. PATENT DOCUMENTS

| | | | | |
|---|---|---|---|---|
| 2,248,734 | A * | 7/1941 | Barr | C07C 1/048 518/706 |
| 3,528,783 | A * | 9/1970 | Haselden | B01J 35/55 422/198 |
| 6,616,909 | B1 * | 9/2003 | Tonkovich | C01B 3/384 423/655 |
| 2006/0099131 | A1 * | 5/2006 | Singh | C01C 1/0441 423/361 |
| 2014/0080076 | A1 * | 3/2014 | Lutz | F23L 7/007 431/253 |
| 2020/0010771 | A1 * | 1/2020 | Yoon | B01D 53/02 |
| 2021/0221753 | A1 * | 7/2021 | Gillespie | B01J 20/226 |

(Continued)

FOREIGN PATENT DOCUMENTS

| | | | | |
|---|---|---|---|---|
| EP | 2682450 A2 * | 1/2014 | | C07C 1/12 |
| EP | 4230287 A1 * | 8/2023 | | B01J 8/001 |

(Continued)

*Primary Examiner* — Jennifer A Leung
(74) *Attorney, Agent, or Firm* — Perkins Coie LLP

(57) ABSTRACT

A modular system is configured to generate renewable fuel. The system includes a modular container that has inlets/outlets and houses a treatment subsystem configured to produce treated water and an electrolysis subsystem configured to perform electrolysis of the treated water to produce hydrogen and oxygen. The modular container further includes a reactor configured to perform an exothermic reaction in as little as a single pass using the hydrogen and carbon dioxide to produce the renewable fuel. The modular container can further include a post-processing subsystem configured to perform further processing of the renewable fuel.

14 Claims, 8 Drawing Sheets

(56) References Cited

U.S. PATENT DOCUMENTS

| | | | | |
|---|---|---|---|---|
| 2021/0364228 A1* | 11/2021 | Bernhardt | ............... | F25J 3/08 |
| 2022/0161222 A1* | 5/2022 | Dahlgren | ............. | B01D 53/965 |
| 2022/0411706 A1* | 12/2022 | Viala | .................... | C12P 5/023 |
| 2023/0282867 A1* | 9/2023 | Pearson | ............. | H01M 8/2475 |
| | | | | 429/400 |

FOREIGN PATENT DOCUMENTS

| | | | | | |
|---|---|---|---|---|---|
| FR | 2977089 | A1 * | 12/2012 | ......... | C01B 13/0207 |
| JP | 2003321400 | A * | 11/2003 | | |
| JP | 2023164202 | A * | 11/2023 | | |
| KR | 10-2014-0084486 | A * | 7/2014 | | |
| WO | WO-2010091831 | A1 * | 8/2010 | ......... | B01D 53/0462 |
| WO | WO-2023210632 | A1 * | 11/2023 | ......... | B01D 53/0462 |
| WO | WO-2023223783 | A1 * | 11/2023 | | |

\* cited by examiner

MODULAR SYSTEM FOR RENEWABLE FUEL GENERATION

BACKGROUND

Utilization of carbon dioxide ($CO_2$) as a feedstock for fuel production as captured from a Direct Air Capture (DAC) system, a byproduct from ethanol production by fermentation, centralized industrial flue gas, or any other point or distributed source is essential for the net reduction of global carbon emissions. The Sabatier reaction is a strongly exothermic process that catalytically converts $CO_2$ with 4 moles of hydrogen to form methane and 2 moles of water. Methane is the critical heating molecule present in natural gas. $CO_2$ re-use offsets usage of fossil-based natural gas. Although the Sabatier chemistry is well known, achieving a cost effective and simple process for a range of process scales, including modular to match with distributed $CO_2$ collection and hydrogen generation production sites, remains lacking.

BRIEF DESCRIPTION OF THE DRAWINGS

Detailed descriptions of implementations of the present invention will be described and explained through the use of the accompanying drawings.

Figure 1:
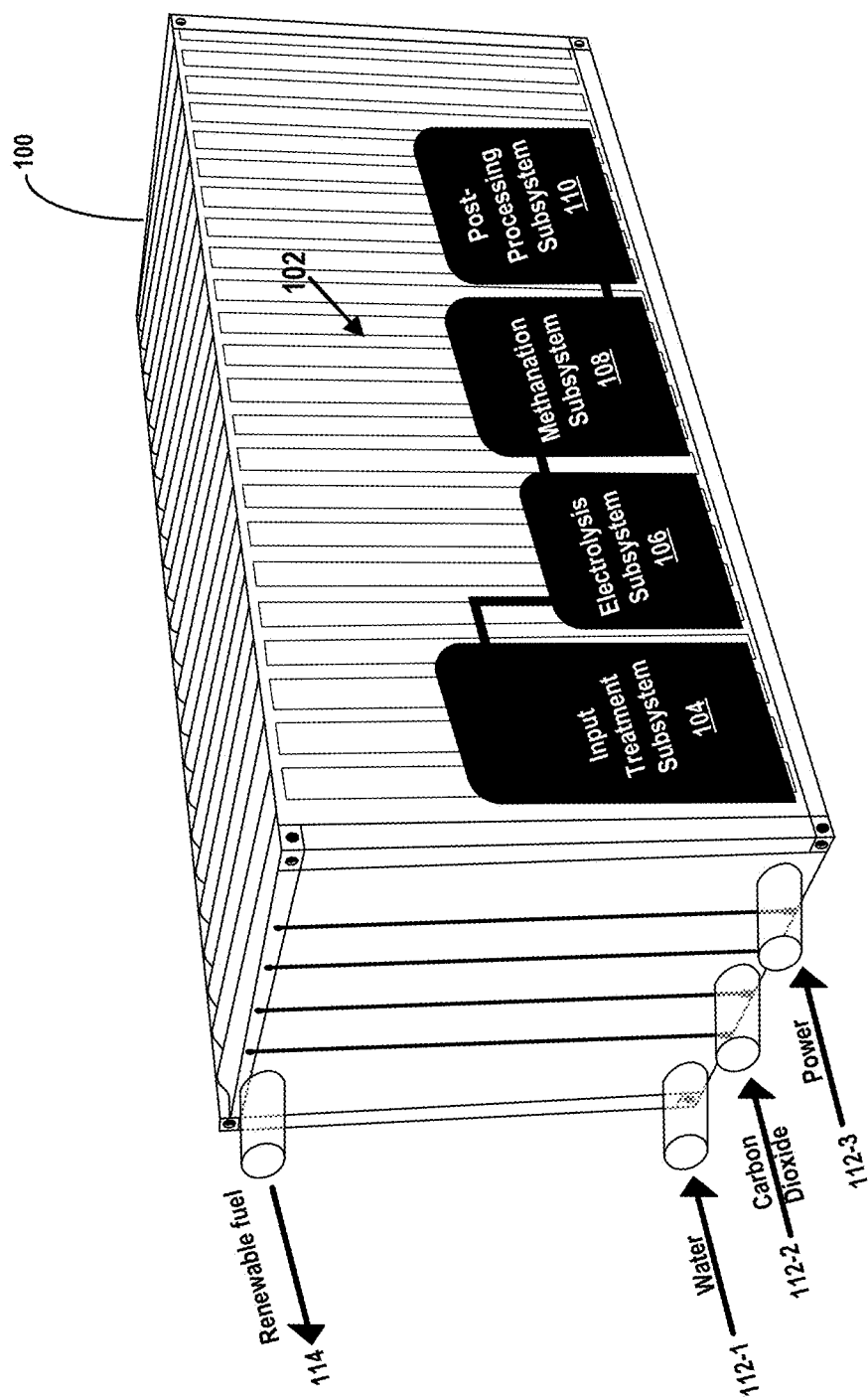
FIG. 1 illustrates a container that houses a renewable fuel generation system.

The technologies described herein will become more apparent to those skilled in the art from studying the Detailed Description in conjunction with the drawings. Embodiments or implementations describing aspects of the invention are illustrated by way of example, and the same references can indicate similar elements. While the drawings depict various implementations for the purpose of illustration, those skilled in the art will recognize that alternative implementations can be employed without departing from the principles of the present technologies. Accordingly, while specific implementations are shown in the drawings, the technology is amenable to various modifications.

DETAILED DESCRIPTION

The disclosed technology includes a system configured to generate renewable fuel. The system can be housed in a container to form a modular unit that can couple the system contained therein to additional containers housing additional systems as needed to scale the production of renewable fuel to a desired quantity. Each modular system can be portable to produce the desired quantity of renewable fuel at various locations. It is generally recognized that the technology may be conducted at any scale of methane production from carbon dioxide ($CO_2$) and hydrogen including non-modular hardware that may be found at centralized or decentralized production facilities.

FIG. 1 illustrates an example of a container 100 that houses the renewable fuel generation system 102 ("system 102"). The container 100 is a physical object that can enclose and/or transport the subsystems and components of the system 102. The container 100 represented in the illustrated example is roughly the size and shape of a shipping container with strength suitable to withstand shipment, storage, and handling of the system 102. Examples of the container 100 can range from large reusable steel boxes used for intermodal shipments to smaller skids or containers that are roughly the size of a household appliance. In the context of shipping the system 102, the container 100 is designed to move the system 102 from one location to another and from one mode of transport to another without unloading and reloading the container or contents therein.

The modular units utilize hardware in a process flow that can treat a wide range of adjacent but different sources and types of input streams and can include infrastructure on the backend that enables a multitude of product forms. The disclosed system can also take substantial advantage of all the materials flowing into it and can capture and utilize coproducts (or byproducts) of the process in a way that retains their value for other applications or for reuse in the same hydrocarbon generation process. For example, FIG. 1 shows that the system 102 includes interconnected subsystems that perform functions or processes to generate the renewable fuel. The subsystems include an input treatment subsystem 104, an electrolysis subsystem 106, a methanation subsystem 108, and a post-processing subsystem 110. The container 100 receives inputs 112 including water 112-1, carbon dioxide 112-2, and power 112-3, and outputs one or more renewable fuels 114. The renewable fuels can include a variety of gas or liquid hydrocarbons or other types of fuels. Examples include synthetic natural gas (SNG), e-natural gas (e-NG), renewable natural gas (RNG), liquefied e-natural gas (e-LNG), and gaseous or liquid oxygen (e-LOX).

The input treatment subsystem 104 can receive water from a source external or internal (not shown) to the container 100. The input treatment subsystem 104 can perform various physical processes on the received water including filtration, sedimentation, demineralization, distillation, biological processes such as the use of slow sand filters or biologically active carbon, chemical processes such as flocculation and chlorination, and the use of electromagnetic radiation such as ultraviolet light.

Generally, the water purification performed by the input treatment subsystem 104 includes the process of removing undesirable chemicals, biological contaminants, suspended solids, and/or dissolved gas from the water. The goal is to produce water that is suitable for renewable fuel generation by the production of green hydrogen from electrolysis. Water purification can reduce the concentration of particulate matter including suspended particles, parasites, bacteria, algae, viruses, and fungi as well as reduce the concentration of a range of dissolved and particulate matter. Processes may include filtration with a filter pore size less than 20 micron or from about 0.2 to 20 microns. A filter of 0.2-microns will substantially remove most biological matter with at least a 3-log or a 3-log to 9-log reduction. Proper purification reduces the electrical conductivity of the water to an acceptable level for the electrolysis subsystem, which may require as low as 5 microsiemens per centimeter (μS/cm), depending on the electrolyzer cell architecture.

The electrolysis subsystem 106 uses direct electric current (DC) to drive an otherwise non-spontaneous chemical reaction to separate elements from naturally occurring sources such as ores or water using an electrolytic cell. The voltage that is needed for electrolysis to occur is referred to as the decomposition potential. The components required to achieve electrolysis are an electrolyte, electrodes, and an external power source (e.g., power 112-3). A partition (e.g., an ion-exchange membrane or a salt bridge) is optional to keep the products from diffusing to the vicinity of the opposite electrode.

The process of electrolysis involves the interchange of atoms and ions by the removal or addition of electrons due to the applied current. Each electrode attracts ions that are of the opposite charge. In this process, electrons are effectively introduced at the cathode as a reactant and removed at the anode as a product. The desired products of electrolysis are often in a different physical state from the electrolyte and can be removed by mechanical processes (e.g., by collecting gas above an electrode or precipitating a product out of the electrolyte). The quantity of the products is proportional to the current, and when two or more electrolytic cells are connected in series to the same power source, the products produced in the cells are substantially proportional to their equivalent weight.

The methanation subsystem 108 includes a methanation reactor that performs a methanation process, which is the conversion of carbon monoxide (CO) and/or carbon dioxide ($CO_2$) to methane ($CH_4$) through hydrogenation. Carbon dioxide methanation has many practical applications. It is a means of $CO_2$ removal from process gas and is also an alternative to preferential oxidation (PROX) in fuel processors for fuel cell applications. Methanation as a means of producing synthetic natural gas (SNG) has been considered as a clean fuel for transportation and/or industrial processes, and as a way to store energy produced from solar or wind power using power-to-gas systems in conjunction with existing natural gas storage and pipelines for transport.

Figure 2:
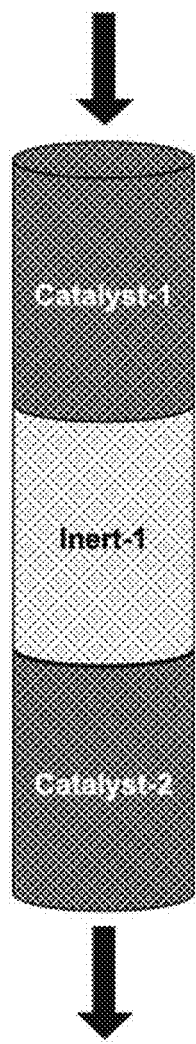
FIG. 2 illustrates a stratified reactor with at least one interspersed inert section.

The present technology includes a stratified methanation reactor that integrates interspersed inert sections between catalyst sections housed within a single reactor vessel. For example, FIG. 2 illustrates a stratified reactor with at least one interspersed inert section of pellets between two fixed-bed catalyst sections. Heat radially transfers through the fixed bed catalyst and inert sections for removal along the wall using active cooling to reduce the temperature of partially reacted gas between catalyst sections for a net reduction of the peak temperature as compared to a reactor that does not contain interspersed inert sections and cooling. The technology may comprise one, two or more inert sections as interspersed between catalyst sections.

The exothermic reaction heat is removed along a wall of the stratified fixed bed reactor by using active heat removal or cooling that may include single phase flow or boiling heat transfer. The wall is defined by the circumference of the interspersed catalyst and inert bed or the wall may include or be cooling channels, coils, or one or more coolant filled tubes that are located within an interspersed bed of catalyst and inert. The temperature rise is moderated in a first section by limiting the first section length and or increasing the catalyst thermal conductivity and or decreasing the catalyst loading in the first catalyst section and combinations thereof. The interspersed inert bed after a catalyst section helps to cool the hot gas effluent using radial heat transfer through the inert particulate section to the colder wall temperature before the gaseous mixture of unreacted feeds and product gas enters a downstream catalyst section. Heat in the downstream catalyst bed may be controlled by limiting the length and or reducing the catalyst loading and or increasing the catalyst thermal conductivity and combinations thereof.

In some examples, there may be one, or two, or more interspersed inert packed bed sections following catalyst sections operating in series. Configurations may comprise a first catalyst section followed by a first inert section followed by a second catalyst section or alternatively a first catalyst section followed by a first inert section followed by a second catalyst section followed by a second inert section followed by a third catalyst section. Any number of catalyst and inert sections may be used although it is generally recognized that it is desirable to limit the number of catalyst inert sections from about 2 to 20 or more preferably from about 2 to 10 for practical implementation. It is also recognized that more than one of the stratified reactors with catalyst beds interspersed with inert may be operated in parallel to achieve a target plant production rate of methane.

The typical fixed bed reactor is made with a hydraulic diameter ranging from about 1-cm to 40-cm, with a preferred diameter ranging from about 2-cm to 15-cm and more preferred hydraulic diameter from about 3 to 10-cm. The total length of the stratified reactor may range from about 0.1-m to 20-m with a preferred length from about 1-m to 10-m. It is recognized that the reactor length will be limited to less than the height of a container for a modular system or can be substantially longer and larger for an industrial process. It is also recognized that the fixed bed reactor can be of a different form factor (e.g., shorter and/or wider) if more active cooling or heat removal tubes, coils, or chambers are employed internally as located in thermal communication to the interspersed catalyst and inert sections to limit the peak temperature.

The following reactions describe the methanation of carbon monoxide and carbon dioxide, respectively:

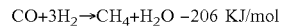

$$CO + 3H_2 \rightarrow CH_4 + H_2O \quad -206 \text{ KJ/mol}$$

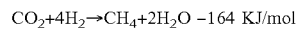

$$CO_2 + 4H_2 \rightarrow CH_4 + 2H_2O \quad -164 \text{ KJ/mol}$$

The methanation reactions are classified as exothermic and their standard heat of reaction is shown. There is disagreement on whether the carbon dioxide methanation occurs by first associatively adsorbing an atom of hydrogen and forming oxygen intermediates before hydrogenation or by dissociating and forming a carbonyl before being hydrogenated. Carbon monoxide is believed to be methanated through a dissociative mechanism whereby the carbon-oxygen bond is broken before hydrogenation with an associative mechanism only being observed at high hydrogen concentrations. A methanation reaction may be conducted over different metal catalysts including but not limited to Ni, Ru, Rh, Pd, Pt, Mo, Re, Fe, Co, Cu and Au or combinations thereof as supported on any high surface area support that may comprise an oxide material such as alumina, titania, zirconia, ceria or other and combinations thereof. These catalyst materials have been widely investigated for the production of methane from a mixture of carbon dioxide ($CO_2$) and hydrogen ($H_2$). Product methane can be used as a fuel gas and produced from a wide range of carbonaceous feedstocks. The product methane may be further used to produce a wide range of derivative chemicals. Nickel is the most widely used catalyst due to its high selectivity and low cost.

Methanation is an important step in the creation of RNG and SNG, which may become clean LNG or compressed natural gas (CNG) to be used in road, rail, air, and marine transport vehicles as a substitute for costly diesel, petrol, etc. Renewable electrical energy can be used to create SNG, for example by electrolysis of water via a proton exchange membrane (PEM) electrolyzer to generate hydrogen, which is then reacted with carbon dioxide from, for example, CSS/U utilization in the Sabatier reaction. The Sabatier reaction (or Sabatier process) produces the product methane and the coproduct water from a reaction of hydrogen with carbon dioxide at elevated temperatures, ranging from about 200 to 800 C with a preferred range from about 300 to 500 C, and more preferably with a wall temperature between 200 C to 400 C and an internal bed peak temperature between 300 C to about 650 C. Pressure may range from about 2 to 200 bara with a preferred range from about 5 to 40 bara in the presence of a catalyst comprising Nickel. For example, referring back to FIG. 1, the methanation subsystem 108 is one example of a hydrocarbon generation subsystem that can be implemented in the system 102 to produce a variety of gas or liquid hydrocarbons that is not limited to methane. As such, the methanation subsystem 108 can be referred to more broadly as a hydrocarbon generation subsystem 108.

The post-processing subsystem 110 can receive gas or liquid hydrocarbons from the hydrocarbon generation subsystem 108 and perform processes to refine the hydrocarbons. In one example, the post-processing subsystem 110 can perform liquefaction of methane gas to produce liquid methane. In an alternate embodiment, the methane as produced can be compressed and stored in a gaseous form. The compression ratio to a stored methane product from the reactor effluent may range from about 1.5 to 100. Additional examples of post processing include removing water as a vapor or liquid after full or partial water condensation or re-pressurizing the hydrocarbons. The post-processing subsystem 110 outputs the gas or liquid hydrocarbons through the outlet 114. The disclosed technology thus generates renewable fuel that can reduce net carbon intensity or emissions compared to conventional sources of fuel. Renewables and energy efficiency, boosted by substantial electrification, can further increase reductions in carbon emissions. In one embodiment, the renewable methane produced from the disclosed process can be introduced into natural gas pipelines for transport or used locally for synthesis or heating purposes.

The description and associated drawings are illustrative examples and are not to be construed as limiting. This disclosure provides certain details for a thorough understanding and enabling description of these examples. One skilled in the relevant technology will understand, however, that the invention can be practiced without many of these details. Likewise, one skilled in the relevant technology will understand that the invention can include well-known structures or features that are not shown or described in detail, to avoid unnecessarily obscuring the descriptions of examples.

Renewable Fuel Generation System

Figure 3:
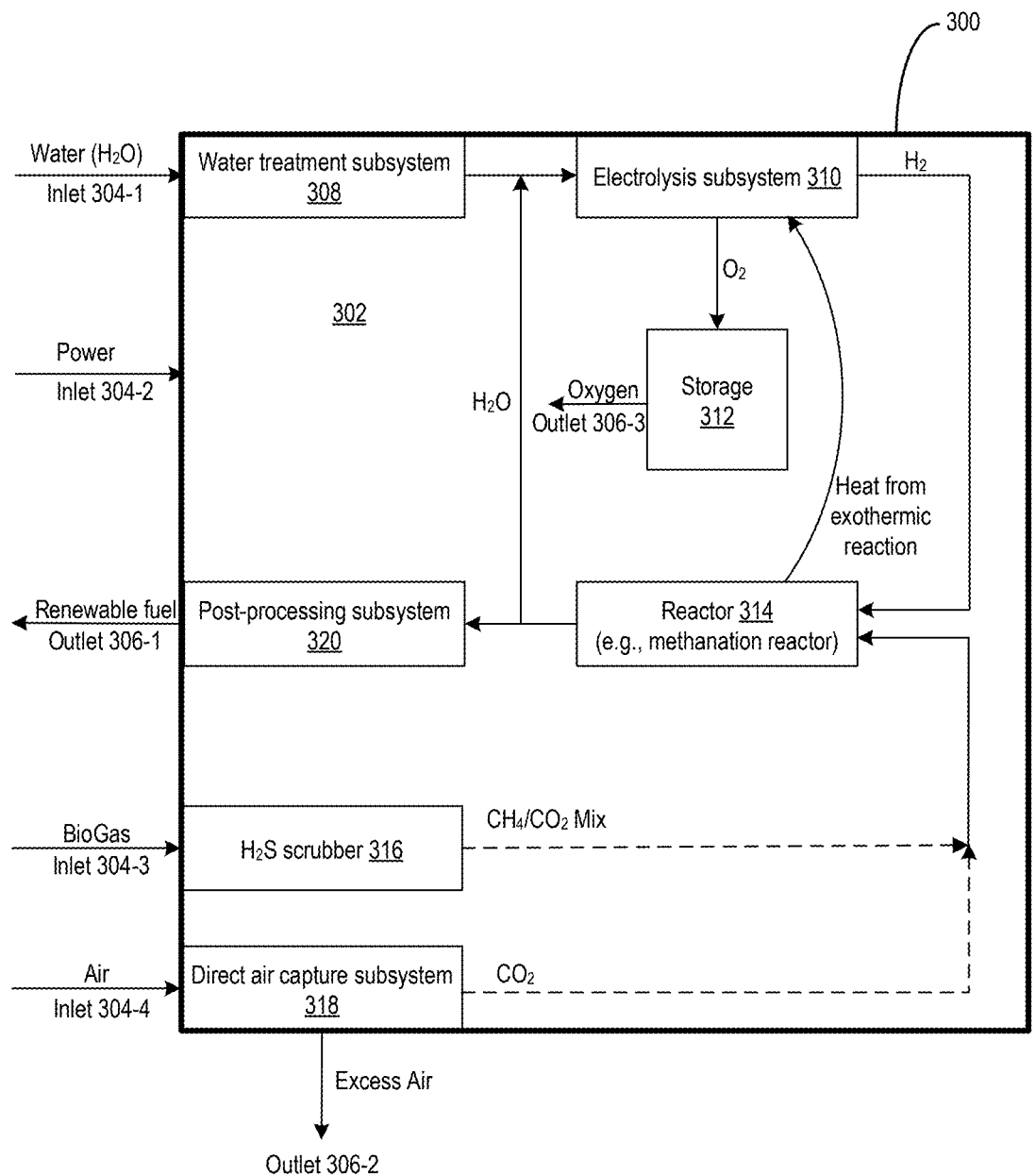
FIG. 3 illustrates components and operations of the renewable fuel generation system.

FIG. 3 is a block diagram that illustrates components of the renewable fuel generation system. A container 300 houses the renewable fuel generation system 302 ("system 302"). That is, the container 300 encloses the subsystems of the system 302. The container 300 has inlets configured to receive inputs used to generate renewable fuel and outlets used to output the renewable fuel and byproducts. As shown, the container 300 includes inlet 304-1 for water (which may be further added to water partially or substantially recovered from the methanation process for a net reduction of fresh water to the process system), inlet 304-2 for power, inlet 304-3 for biogas, and inlet 304-4 for air (collectively and individually referred to as "inlet(s) 304"). The container 300 is shown to include an outlet 306-1 configured to output to one or more renewable fuels. The renewable fuels can include a variety of gas or liquid hydrocarbons (e.g., natural gas, liquefied natural gas) and/or other products such as gaseous or liquid oxygen. An outlet 306-2 is configured to output other coproducts or air. The container 300 can include additional or fewer inlets or outlets that are not shown for the sake of brevity. The container 300 is modular and, in some implementations, portable to enable moving the container to locations where generating renewable fuel is desired. The container is not necessarily intended to be moved frequently but rather deployed in diverse locations and scaled as needed.

The container 300 encloses a water treatment subsystem 308 that is configured to receive water from the inlet 304-1 and process the water to produce treated water. The water treatment subsystem 308 can perform multiple processes to treat water input to the container 300. Examples of the multiple processes include a physical process including filtration, sedimentation, or distillation; a biological process including slow sand filters or biologically active carbon; and/or a chemical process including flocculation, chlorination, or electromagnetic radiation. The water treatment subsystem 308 can optionally perform a pumping process to increase the pressure of the treated water input to an electrolysis subsystem 310.

The electrolysis subsystem 310 is configured to receive the treated water from the water treatment subsystem 308, receive the power from the inlet 304-2, and utilize the power to perform electrolysis of the treated water to produce hydrogen and oxygen. The electrolysis subsystem 310 may be of a type that is supported at high temperature as defined from about 35 to 700 C depending on the type of electrolysis equipment employed. That is, heating the electrolysis subsystem 310 can improve the efficiency of electrolysis reaction.

A reactor 314 (e.g., methanation reactor) is configured to receive the hydrogen from the electrolysis subsystem 310, receive the carbon dioxide alternatively from either the inlet 304-3 or 304-4 at any point in time, and perform an exothermic reaction using the hydrogen and the carbon dioxide to produce a renewable fuel (e.g., methane gas) and coproducts (e.g., water and heat). The reactor 314 can transfer the heat produced from the exothermic reaction to the electrolysis subsystem 310 via the use of a heat transfer fluid in thermal communication between the two systems. The electrolysis subsystem 310 can increase the efficiency of the electrolysis reaction with part or all of the excess heat transferred from the reactor 314. The reactor 314 can also transfer water produced at the methanation reactor 314 to the electrolysis subsystem 310 or the water treatment subsystem 308. The electrolysis subsystem 310 is thus configured to use none, part, or all of the water from the reactor 314. The process performed by the system 302 can be described as hydrogenation, which includes but is not limited to methanation. The hydrogenation process can include most $CO_2$-to-hydrocarbon processes for a variety of applications.

An example of the reactor includes a stratified interspersed inert methanation reactor, which has a reaction bed with a stratified arrangement of regularly or irregularly alternating sections of different types of media and active heat removal. In one example, the types of media include catalyst material (e.g., a transition group metal, a platinum group metal, or nickel-based catalysts) and inert material. In one example, each section of catalyst material has a boundary in common with at least one section of inert material. The active heat removal encompasses both the catalyst section and the inert section such that the temperature of the mixture of partially reacted gas is reduced substantially in the inert section after one catalyst section prior to entering the subsequent catalyst section. A substantial temperature reduction ranges from about 10 C to 400 C with a preferred temperature reduction from about 50 C to 250 C.

A reactant chamber can include a first catalyst section that traverses at least a portion of the full length of the reaction bed, through which a mix of hydrogen and $CO_2$ flow to perform the exothermic reaction in a "single pass" such that reactants only flow through the reactor a single time, as opposed to multi-pass systems where reactants flow multiple times in a loop or through a series of reactors or are recycled several times in the same reactor. The reactor 314 can include multiple reactant channels comprising the interspersed catalyst and inert beds as operated in a single pass, where the number of reactant channels depends on a desired flow rate and/or temperature limit. In one example, the reactor 314 includes one or more coolant tubes configured to pass coolant fluid to cool the temperature of the reaction bed.

The inert material can include a high thermal conductivity substantially inert material such as SiC, dense alumina, Al, Cu, or others and combinations thereof where the thermal conductivity ranges from about 3 W/m-K to 300 W/m-K, with a preferred range from about 10 to 120 W/m-K. In another embodiment, the inert material can include a sorbent material configured to retain a gas comprising water vapor through absorption or adsorption. That sorbent can be "regenerated" in response to a temperature or pressure swing to remove the excess water when the sorbent reaches a threshold capacity (e.g., when unable to absorb or adsorb more water). In one example, water vapor is produced as a byproduct of the exothermic reaction and stored in the sorbent material.

A post-processing subsystem 320 is configured to receive products from the reactor 314 and perform one or more processes to refine the products or remove coproducts. For example, the post-processing subsystem 320 can perform liquefaction of methane gas and output the liquefied methane as the renewable fuel through the outlet 306-1. In other examples, the post-processing subsystem 320 can remove water vapor or other coproducts in addition to or instead of performing liquefaction. Additional options for the post-processing subsystem 320 include separation (if creating a liquid product) or re-pressurization (for bottling or injection), or product drying and cooling. The system 302 optionally includes an oxygen storage container 312 configured to receive oxygen output by the electrolysis subsystem 310. The system 302 includes an outlet 306-3 configured to export the oxygen stored in the storage container 312.

The system 302 can optionally include a scrubber subsystem 316 (e.g., $H_2S$ scrubber) that is configured to receive biogas from the inlet 304-3 as the feedstock including carbon dioxide and perform a scrubber process of the biogas to filter for volatile compounds and partially purify the carbon dioxide. In another option, a direct air capture subsystem 318 includes a porous, solid-phase sorbent material and is configured to receive ambient air as the feedstock including carbon dioxide. The direct air capture subsystem 318 performs a sorbent-based processing of the air to extract the carbon dioxide and expel excess air through an outlet 306-2. Examples of the sorbent material include a porous, solid-phase sorbent material (e.g., mesoporous silicas, zeolites, or metal-organic frameworks). Using the porous, solid-phase sorbent material is more efficient than using amine gas treating processes for selectively removing carbon dioxide from feedstock.

Multiple containers including respective systems can be coupled to produce a desired amount of renewable fuel, which can be scaled in proportion to a number of the multiple interconnected modular containers that are concurrently or intermittently operating. The systems of the multiple containers can be grouped in different subsets that operate at alternate times to continuously produce the renewable fuel. In one example, the multiple containers are communicatively coupled to a controller of the multiple modular containers to generate a desired amount of renewable fuel at a desired location, that may match the intermittency of renewable power.

Figure 4:
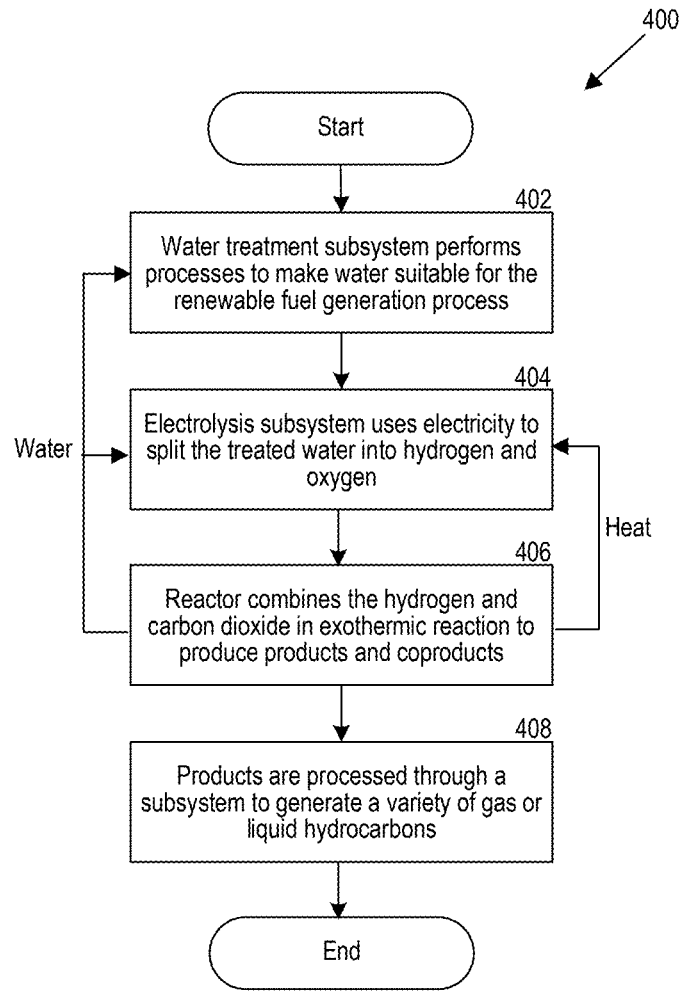
FIG. 4 is a flowchart that illustrates a process performed to generate renewable fuel by a system enclosed in a modular container.

FIG. 4 is a flowchart that illustrates a process 400 performed to generate renewable fuel by the system enclosed in a modular container. The various physical components that are subsystems or parts of subsystems are configured to receive the inputs from external sources through inlets or from outputs of other subsystems. The physical components are enclosed partially or fully in respective containers such that only inputs and outputs cross the boundary of the container. The subsystems are interconnected to perform a series of operations that start with reagents and end with renewable fuel and byproducts. The byproducts output by some subsystems can be fed as inputs to other subsystems as reagents or fuel to perform processes or operations. As such, the system can reduce waste from component subsystems and maximize efficiencies.

At 402, the water treatment subsystem receives water supplied through the inlet of the container and performs one or more processes to make the water suitable for the renewable fuel generation process. In one example, the water treatment subsystem 408 operates to filter and sufficiently purify the water through a filter and/or distillation column.

At 404, the treated water is pressurized from about 1 bara to 40 bara with a preferred range from about 1 to 30 bara and supplied to an electrolysis subsystem that performs electrolysis, which uses electricity to split the treated water into two gas streams substantially comprising hydrogen and oxygen. The electricity is input through an inlet to the electrolysis subsystem, which outputs hydrogen and oxygen as products of the electrolysis reaction. The electricity can be supplied from grid, intermittent or stored renewable or nuclear sources to produce low-emission products. The oxygen can be liquefied and stored at an oxygen storage tank. The liquid or gaseous oxygen stored in the storage tank can be directly used for various purposes or combined with another product to perform an oxidation reaction that creates complex hydrocarbons or used to enhance growth rates in biological conversion reactors, including fermentation.

At 406, the hydrogen that is output from the electrolysis subsystem flows into the reactor to perform an exothermic reaction (e.g., methanation reaction). The reactor combines the hydrogen and carbon dioxide in an exothermic reaction that produces hydrocarbons and coproducts including water and heat. The excess heat generated from the exothermic reaction can be transferred in part or full to the electrolysis subsystem, which uses the heat to improve the overall efficiency of the electrolysis reaction.

In one example, the reactor performs a methanation reaction using hydrogen and carbon dioxide. The source of the carbon dioxide can include a point-source, which is any single identifiable source of pollution from which pollutants are discharged, such as a pipe, ditch, ship, or factory smokestack. In one example, the source of the carbon dioxide is a biogas from a dairy, animal operating facility, landfill, or wastewater treatment plant. The source material is input through, for example, an $H_2S$ scrubber, which performs a process to filter the source material for volatile components and then feeds the scrubbed gas into the reactor to perform the methanation reaction.

In another example, a direct air capture subsystem captures ambient air through the inlet of the container to extract the carbon dioxide. The direct air capture subsystem can include a sorbent-based direct air capture subsystem that extracts at least a portion of carbon dioxide from the captured air and feeds the carbon dioxide into the reactor for performing methanation reactions. Examples of solid sorbents for carbon capture include porous, solid-phase materials such as mesoporous silicas, zeolites, and metal-organic materials. The sorbents can function as more efficient alternatives to amine gas treating processes for selectively removing carbon dioxide from large, stationary sources including power stations. Coproducts of the extraction process can include excess air, which is output to the atmosphere through the outlet. The output products of the reactor include renewable hydrocarbons and water.

At 408, the generated products are processed to produce the desired renewable fuel. For example, a post-processing subsystem can receive products from the reactor and perform one or more processes on the products including liquefaction, removal of water vapor or other coproducts, re-pressurization, drying, or cooling. In one example, SNG is processed through a liquefaction subsystem to generate clean LNG. The water that is produced from the exothermic reaction can be sent to the electrolysis subsystem as a feedstock for the electrolysis reaction to generate separate streams comprising hydrogen and oxygen.

As indicated earlier, the container that houses a renewable fuel generation system is modular and optionally transportable. As such, the container is a self-contained unit that houses a renewable fuel generation system, which can be placed in a variety of locations to provide renewable fuel as needed. The container can provide renewable fuel temporarily or permanently at one or multiple locations, at different times. In addition, the containers can be assembled in an array of interconnected renewable fuel generation systems to scale an amount of renewable fuel that is desired at a particular location. That is, colocating containers in a common location can increase the amount of renewable fuel generated in proportion to the number of containers.

The modular design of each unit allows for adapting to a variety of applications because each unit is deployable at a significantly more flexible or smaller scale compared to conventional fuel generation systems. For example, a group of units can operate in parallel to produce a desired volume of product as required for a specific application. The group of units can be fed common inputs of feedstock of a variety of types and output streams of product from one or multiple units. In contrast, conventional fuel generation systems are designed as site-specific and application-specific structures that are not modular. Hence, conventional systems are not widely available for commercial applications because they are not deployable at different locations due to being designed for specific locations and conditions. It is recognized that the present embodiments may be applied to modular technology, and may also be used at larger and or non-modular scales and at any size production facility.

Figure 5:
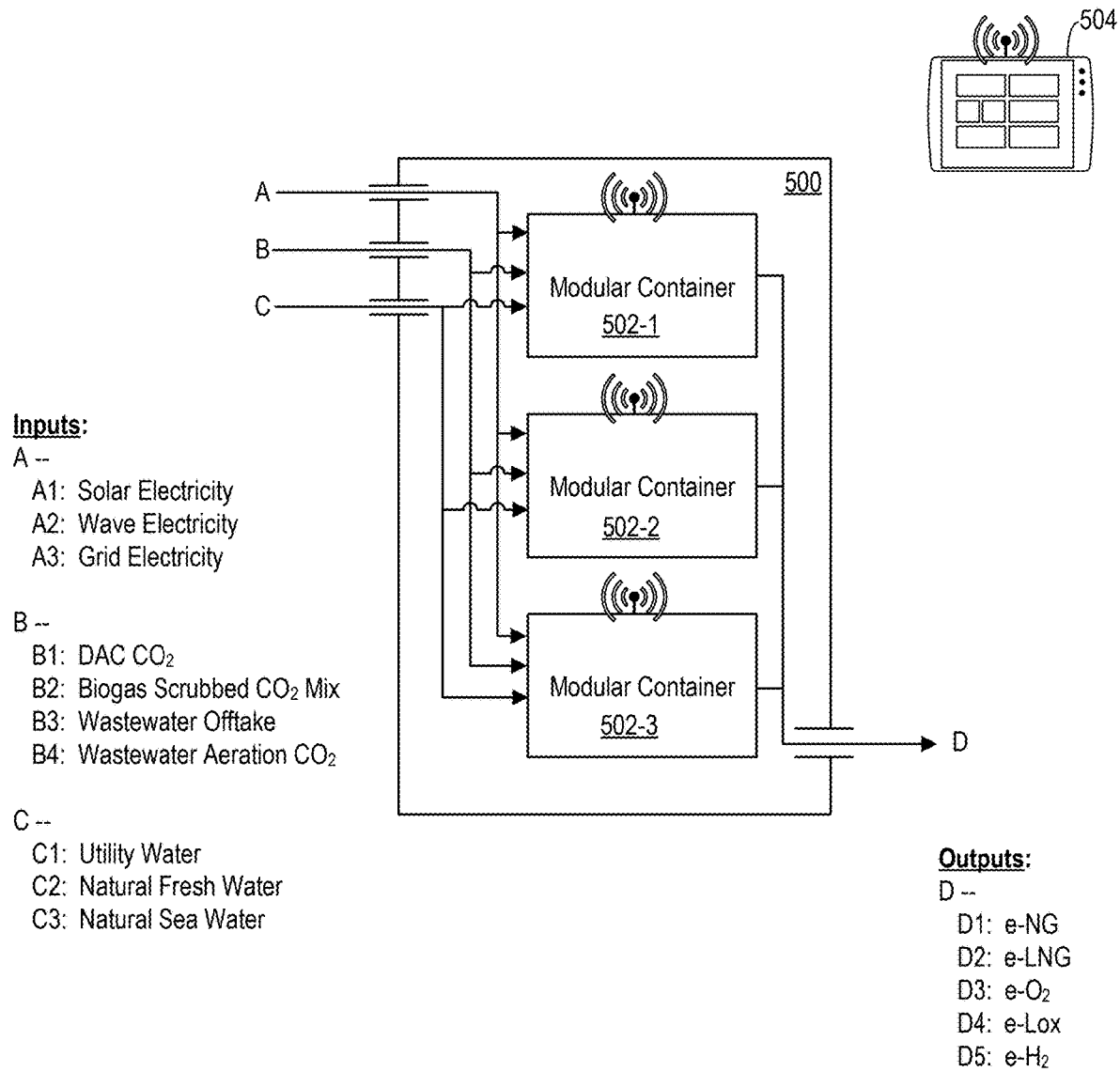
FIG. 5 illustrates an example of a modular deployment of multiple renewable fuel generation systems.

FIG. 5 is a block diagram that illustrates an example of a modular deployment of multiple renewable fuel generation systems at a common location. As shown, the location 500 is any suitable area on which the modular containers 502-1 through 502-3 (collectively referred to as "containers 502" and individually as "modular container 502") can be deployed. That is, the location is anywhere that renewable fuel generation is desired (e.g., near equipment or a manufacturing plant) and that can support containers. The containers 502 can be housed inside of another structure or in an open-air environment. Each of the containers 502 includes a renewable fuel generation system as described in FIGS. 1-4. The containers 502 are each fed inputs including A, B, and C and output renewable fuel D.

The input A is a power source such as solar electricity (A1), wave/hydro-generated electricity (A2), wind (not shown), or electricity from the grid (A3). Other sources of renewable power with a low carbon footprint can include surplus nuclear power. The input B is a source of carbon dioxide such as that from direct air capture (DAC) (B1), a biogas scrubbed mix (B2), wastewater offtake (B3), or wastewater aeration (B4). The input C is a source of water such as from a utility (C1), natural fresh water (C2), or natural sea water (C3). As shown, the inputs A, B, and C are distributed to each of the containers 502, which then output renewable fuel such as e-NG, RNG, e-LNG, e-$O_2$, e-LOX, or e-$H_2$. As shown, the modular components can be controlled remotely from a common computer 504 that controls and monitors operations of the containers 502. For example, an operator of the computer 504 can turn any of the containers 502-1, 502-2, and 502-3 on/off to achieve a desired production of renewable fuel. In one example, the computer 504 can wirelessly communicate with the container 502. Another example of the computer 504 includes the computer system described below.

The computer system and control valves maximize the product yield of the system by modulating the flow of reactants into one or more reactors based on measured performance parameters. Any computer system can be used including but not limited to on/off operation, or a programmable logic controller with feedback control based on measured temperature, pressure, and or composition. Parameters may be set to ensure optimized production and to protect for catalyst longevity. In one embodiment, where a material utilized in the reactor bed may have limited capacity (such as catalyst life or an inert water vapor sorbent), the computer system can be utilized to switch reactant flow to another reactor when the first reaches capacity or needs regeneration. During this period, the material in the first reactor may be regenerated via change in pressure, temperature or gas feed composition, and then returned to operation. This swing-bed operation allows for continuous generation of end-product, and flexibility for variable and intermittent energy supply which is common with renewable electricity sources.

The modular units are designed as fungible systems but can be customized to have different sizes and capacities for different applications, such as mobile factories. The modularity allows for connecting modular units of different sizes and capacities as needed to produce a desired volume of product. In contrast, conventional e-fuel deployments are intended to validate some internal technology or conceptual approach and are not designed with the intention of maximizing the value stream from a mass-deployment, commercial perspective. As such, the disclosed technology can generalize, modularize, and make ubiquitous a process that currently only exists in limited forms and has a noncommercial utility. It is recognized that the modular system can be deployed at any scale and is not limited to a container.

Stratified Interspersed Inert Methanation Reactor

The disclosed methanation reactor has an architecture and performs operations that integrate multiple heat and conversion efficiency management techniques. For example, prior methanation reactors vary by design but generally use adiabatic reactor beds in which heat is generated by the exothermic reaction but does not substantially leave the reactor in the radial direction other than through modest heat losses. Heat generated by the exothermic methanation in these traditional adiabatic reactors exits with the effluent gas that is at a substantially higher temperature than the inlet feed stream. The beds include a tube of pellet catalyst at a fixed inlet pressure, which is prone to hot spots, and the reactors require multiple sequential beds with intervening separate heat exchangers that may comprise hardware configurations such as shell and tube, plate and frame, microchannel, or other for reliable efficiencies.

Further, prior reactors can include actively cooled fixed beds where, for example, coolant flows as part of a separate pneumatic system for temperature management. Other reactor designs use microchannel beds or magnetic induction heated beds, which are impractical in modular and/or portable configurations due to the complexity of those structures. The disclosed reactor innovates over prior designs with a novel architecture and operation in a way that allows for reliable, scaled operations, and improves thermal management and single-pass conversion, which results in improved unit economics compared to prior systems.

Figure 6:
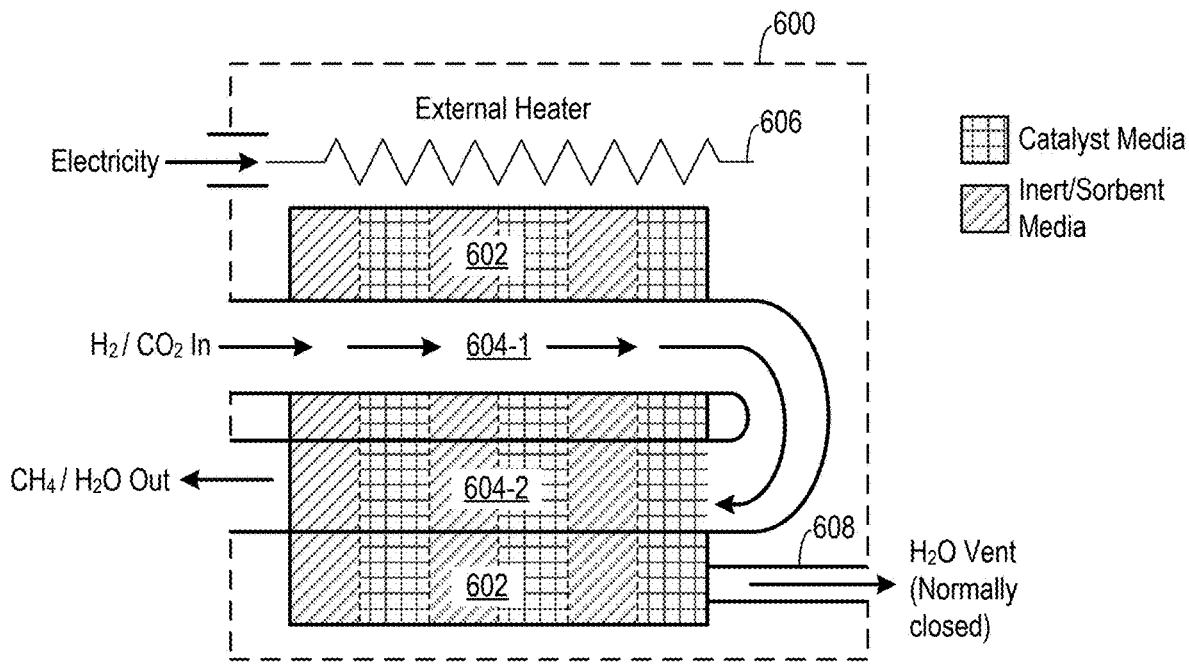
FIG. 6 illustrates one embodiment of a cross-section of a stratified methanation reactor of the renewable fuel generation system.

FIG. 6 is a block diagram that illustrates a cross-section of one embodiment of a stratified interspersed methanation reactor ("reactor") for the renewable fuel generation system. The reactor 600 has a reaction bed 602 that has regularly or irregularly interspersed sections of catalyst media and inert media in fixed locations within a tubular or plate reactor that includes active cooling (not shown). Active cooling may include air, a gas that may comprise an effluent stream from a process, a fluid that boils fully or in part, or a high specific heat capacity heat transfer fluid such as a hot oil or other material that can remove heat from the highly exothermic reaction both from catalyst sections and from interspersed inert sections. As shown, each section of catalyst media has a boundary in common with at least one section of inert media. The catalyst media increases the rate at which the reactants (e.g., hydrogen, carbon dioxide) undergo a methanation reaction without the media undergoing a permanent chemical change. Examples of a catalyst media include transition group metals or platinum group metals (e.g., cobalt, iron, platinum, palladium, rhodium, ruthenium, iridium, and osmium) or nickel-based catalysts, which are beneficial for industrial applications due to their low cost and relatively high activity.

The inert media is a solid substance that is not substantially chemically reactive. It is recognized that the inert material may have some residual background activity such that the conversion of CO2 within each inert section is less than about 10% and preferably in the range of about 0 to 2% and more preferably from about 0 to 0.5%. In one embodiment, the inert media is of an equal or higher thermal conductivity than the catalyst material to promote heat removal. In another embodiment, the inert media includes a sorbent, which is an insoluble material or mixture of materials used to recover water vapor through the mechanism of absorption, or adsorption, or both. Here, the sorbent material can absorb and store excess water vapor that is generated as a byproduct of the exothermic methanation reaction. Absorbing the water can improve reaction kinetics and single-pass efficiency.

The stratified interspersed reactor includes a first catalyst section comprising a fixed bed catalyst pellet or pelletized media that may be made from a traditional pellet ranging from about 1-mm to about 20-mm in hydraulic diameter with a preferred range from about 3 to about 10 mm. The catalyst pellet is internally porous such that reactants diffuse inward to reacting sites and products diffuse outwards to the bulk fluid that flows past pellets that substantially fill the cross section of the catalyst section in the fixed bed reactor. Catalyst shapes may be spherical, cylindrical as formed by extrusion, or any geometric shape that may include Raschig rings, tri-lobes, or other structures. In an alternate embodiment, the active catalyst may be coated on the outside of a catalyst to form an egg-shell structure or may be contained within the central core of the catalyst structure to form an egg-yolk configuration or any combination thereof. Any shape or type of catalyst may be used in each catalyst section. A substantially filled cross section recognizes the void fraction that is achieved by a fixed bed catalyst and may range from about 0.3 to about 0.55 with a preferred range from about 0.35 to about 0.45. It is recognized that the local void fraction near the surface of a tube wall may be higher due to the irregular packing of a particulate catalyst in a tubular reactor but that there is not a substantial open region where flow is favored that minimizes flow through the packed bed catalyst section.

In one embodiment, at 604-1 the reactant stream is preheated in part or full by transferring heat from the hot effluent gas exiting the inventive reactor configuration. Thermal recuperation may occur in a separate gas-gas heat exchanger. In an alternate embodiment, transfer of energy between the hot product effluent stream and colder incoming feed stream may be configured within the inventive reactor system by the use of a change in flow direction such as a U-bend or similar, in order to heat the stream of reactants before flowing into the first catalyst section.

At 604-2, a first inert section is immediately downstream from the first catalyst section as housed within a fixed bed reactor chamber. The inert media may take the same geometric form as the catalyst or may use a different geometry. In one embodiment, the catalyst may be an extrudate where the inert section contains a tablet form or any combination thereof. The inert material preferably has a thermal conductivity higher than the catalyst to improve radial heat transfer to the wall. In one embodiment, the inert media or pellet is substantially dense to provide a higher thermal conductivity whereas the catalyst pellet may have internal porosity for accessible reaction sites and as such a porous material will have a lower effective thermal conductivity than a dense material. In one embodiment, the catalyst pellet will take a hybrid form that is partially dense and partially porous in different radial regions of the pellet.

It is recognized that there may be an intervening porous agent between the catalyst and inert sections that is a fraction of the length of the inert section length, ranging from about 0 to about 0.1 and more preferably from about 0 to about 0.01 of the inert section length. This intervening porous layer may be used to fixture and separate the catalyst and the inert pellet media. The shape, size and density of the catalyst and inert material may differ from each other, and it may be advantageous to place a porous frit, foam, gauze, screen, quartz wool or similar porous media between intervening layers of interspersed catalyst and inert to minimize inert and catalyst material mixing during reactor loading operations and/or during operation and/or during transport from a loading location to an operating site. It is generally recognized that the use of the intervening porous agent between the catalyst and inert section still defines a common boundary between the catalyst and inert section.

The sections of catalyst and inert share a common heat transfer wall as separated in axial location. The heat transfer medium may flow in a counter-current, co-current, cross-current, and or combinations thereof past the interspersed catalyst and the inert sections such that heat as generated from the highly exothermic Sabatier reaction is removed from both the catalyst and inert section to reduce the peak temperature in each catalyst section. The heat transfer medium may be a fluid that enters the reactor from about 150 C to 450 C with a preferred temperature from about 200 to 380 C. The temperature rise in the heat transfer medium may range from about 1 C to about 50 C with a preferred range from about 1 to about 10 C. The volumetric specific heat capacity of the heat transfer medium as defined by the specific heat capacity Cp in KJ/kg-C multiplied by the heat transfer fluid density in kg/m3 is substantially higher than the volumetric specific heat capacity of the gaseous feed and product stream by a factor of 2× or more such that the temperature rise in the heat transfer medium is substantially less than the temperature change in the reacting gas by a factor of 2× or more. In an alternate embodiment, the heat transfer medium may be a fluid that undergoes partial or full boiling at a temperature from about 100 to 500 C and the temperature rise of the boiling fluid is from about 0 to about 50 C. The boiling fluid may undergo boiling followed by superheating within the coolant chamber to remove the exothermic reaction heat. In an alternate embodiment, the heat transfer medium is a gas that flows at a sufficient velocity to remove the heat released from the highly exothermic reaction. The cooling gas may enter from a temperature of about 25 C to 400 C and the temperature rise may range from about 50 to 500 C.

The configuration of the stratified interspersed inert reactor and cooling channels may be shell and tube where the heat transfer coolant medium flows in either the shell or the tube side. The configuration may be plate and frame where the coolant medium flows in interleaved layers between the stratified interspersed inert chambers. The configuration with coolant may take other forms where the catalyst and inert beds are interspersed such that heat is removed through these sections with a cooling media in thermal communication with both.

The reactor can include multiple single pass channels or tubes operating in parallel to produce a desired amount of renewable fuel. The quantity of channels or tubes may be numbered up to produce a target production rate of the renewable fuel. A tradeoff between the number of parallel tubes and fewer but larger tubes is a function of limits on a reactant flow rate, pressure drop, and/or peak temperature for the catalyst or heat transfer media. That is, the number of channels or tubes can depend on flow rate and thermal needs (e.g., temperature limits). One or more coolant channels (e.g., tubes or open flow plenum) are used to carry coolant fluid that passes in thermal contact with the reaction bed 602 and the inert sections.

The arrangement of regularly or irregularly alternating substantially inert media disburses the reaction sites in alternating areas across the reaction bed, allowing for a more consistent thermal profile along that axis as coupled with active cooling to remove all or part of the exothermic heat generated by reaction, which improves catalyst performance and longevity by, for example, reducing or eliminating hot spots that otherwise occur in reaction beds that are not stratified with interspersed inert sections and active cooling. As such, the methanation reaction occurs at alternating points along the bed, which moderates the temperature rise across the bed. The consistent thermal profile or a profile with a smaller temperature rise than a comparative case without interspersed inert with active cooling can be achieved because the sections of media have equal or unequal lengths or occupy equal or unequal volumes along the reaction bed 602 that is traversed by the reacting fluid.

In an alternate embodiment, the heating element 606 can increase a temperature of the reaction bed 602 to initiate the exothermic methanation reaction and deactivate at a point at which the reactor generates enough heat to sustain generation of renewable fuel using heat produced by the exothermic methanation reaction.

Figure 7:
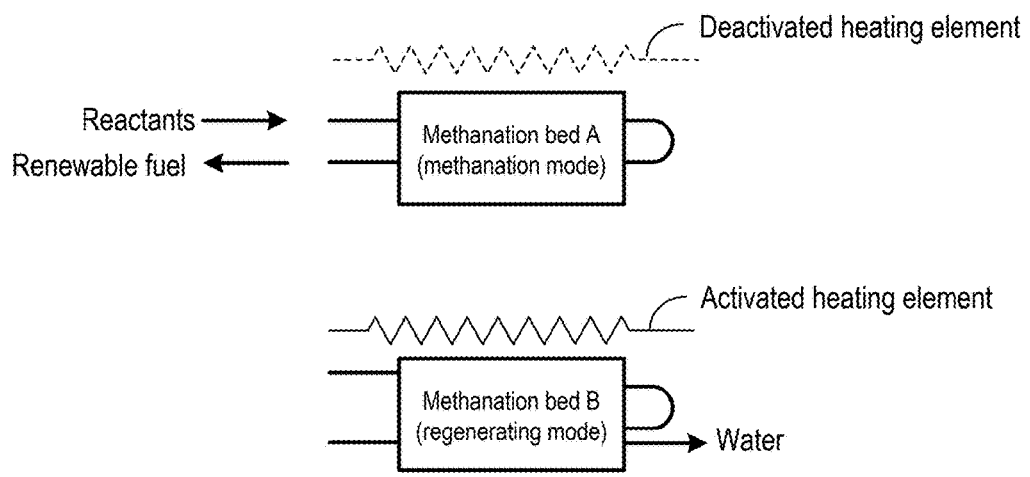
FIG. 7 illustrates a swing bed operation for the renewable fuel generation system.

In an alternate embodiment, the heating element 606 can activate periodically to remove sorbed material in the reaction bed 602 by expelling water from a sorbent material in the inert media section of the bed. The water can then be expelled from the reactor. An outlet 608 can be configured to vent water extracted from this sorbent material to an environment external to the reactor. For example, the heating element 606 can activate periodically to remove water from a sorbent material while processes for generating renewable fuel are deactivated. FIG. 7 is a block diagram that illustrates a swing bed operation for the renewable fuel generation system. In the illustrated example of a swing bed operation, methanation beds A and B are configured to perform different operations at the same time. That is, each reaction bed performs a methanation reaction at one period and performs a desorb process to expel water from the reactor at a different period. As such, a methanation reaction of at least one equivalent reactor is operated continuously while other reactors of a group are operated to desorb water from its sorbent material. In one example, a group of methanation reactors are configured to operate at alternate periods to optimize performance of the group to continuously generate a desired amount of renewable fuel. The reactors cycle between methanation and regenerative modes.

Figure 8:
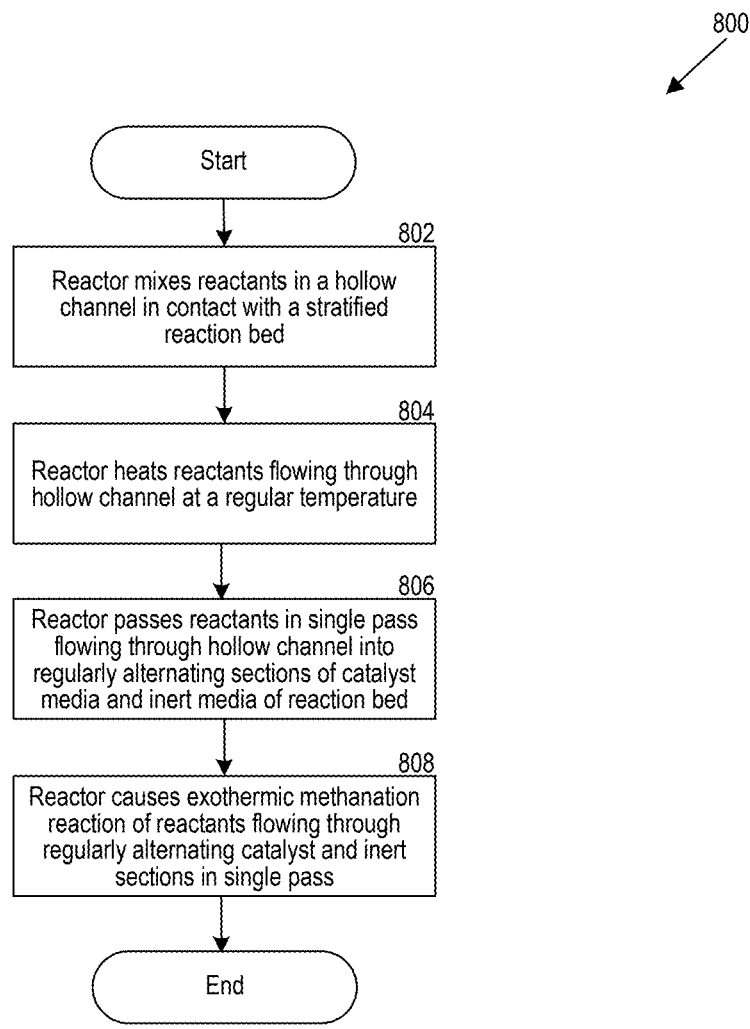
FIG. 8 is a flowchart that illustrates a process performed by a stratified methanation reactor to generate renewable fuel.

FIG. 8 is a flowchart that illustrates a process 800 performed by a stratified interspersed methanation reactor ("reactor") to generate renewable fuel in a single-pass process. The reactor uses reactants comprising hydrogen and carbon dioxide received at the reactor inlet to generate renewable fuel (e.g., methane) and coproducts including water and heat. The coproducts can be reused to reduce system waste and increase efficiency. For example, the water produced by the methanation reactor can be fed in part or full to an electrolyzer that produces hydrogen reactant for the reactor.

At 802, the reactor mixes reactant streams of hydrogen and carbon dioxide with at least a portion of a reaction bed having alternating sections of catalyst media and inert media in fixed locations along the channel length. The reaction bed is arranged such that each section of catalyst media has a boundary in common with at least one section of inert media. The boundary may comprise a short porous region to aid the physical separation of the catalyst and inert media. For example, a section of catalyst media (or inert media) is sandwiched between sections of inert media (or catalyst media). The reactants flowing through the reaction bed in a single pass react to form methane.

At 804, the reactor partially or fully preheats the reactants flowing upstream of the catalyst bed in a single pass at a regular temperature that is maintained due to the alternating sections of catalyst media and inert media. That is, having alternating sections of catalyst material between inert material as coupled with active heat removal using a heat transfer media in thermal contact with the catalyst and inert interspersed section mitigates hot spots that would otherwise result if the reactor were operated with catalyst material alone.

At 806, the reactor passes the reactants into the regular or irregular alternating sections of catalyst media and inert media. That is, the heat exchange medium preheats the reactants from the heat generated by the reaction bed or from a separate heater (e.g., electric heater) upstream of the reactor chamber.

At 808, the reactor causes an exothermic methanation reaction of the reactants flowing through the regularly or irregularly alternating sections of catalyst media and inert media. That is, the preheated mix of hydrogen and carbon dioxide reacts with the catalyst media to generate methane and byproducts of water and heat from the exothermic reaction.

In one embodiment, prior to causing the exothermic methanation reaction, a heating element can initiate the exothermic methanation reaction.

Example 1

Methane or renewable natural gas (RNG) is produced from carbon dioxide and hydrogen using a Nickel-based catalyst. The reaction is highly exothermic and prone to large hot spots that reduce catalyst life. Further operating the reactor at a high temperature promotes the formation of unwanted carbon monoxide (CO). The inventive process integrates thermal enhancement of inert beds interspersed between catalyst beds within a fixed bed reactor to reduce peak catalyst temperature with the use of active cooling for all sections. The number of interspersed inert beds is one or two, although generally recognized that more interspersed stages could further improve performance.

One example catalyst is based on a 20 wt % Ni supported on alumina. A microkinetic model for the described catalyst was published by Schmider, Maier, and Deutschmann, 2021. The kinetic model and associated reaction parameters are based on 42 fully reversible reaction steps. The model was evaluated in a fixed bed reactor and published by Shirsath et al 2023 for a 17 wt % Nickel on alumina catalyst. Shirsath used a slightly cooled inlet feed gas and co-mixed the catalyst bed with a high thermal conductivity SiC in a 4:1 mass ratio in a single section while still producing an exotherm exceeding 100 C in the first 5-mm of reactor length using a narrow diameter lab-scale reactor tube (6-mm). The $CO_2$ conversion reported by Shirsath approached about 80%. From analysis of the published Shirsath data, a conversion factor for the ratio of FCatGeo/Catalyst loading in kg/m3 of 0.285 was obtained and used with the microkinetic model. An inventive operating window is determined using interspersed inert sections between catalyst sections with active cooling for practical reactors with substantially larger tube diameters as practical for scaling this highly exothermic reaction.

Reactor diameters of 0.05-m or 0.08-m are investigated for a catalyst pellet and inert pellet diameter of 5-mm. The tube wall is held constant as achievable with boiling heat transfer or the use of a liquid heat transfer medium such as a hot oil in a multi-tubular fixed-bed reactor. The microkinetic model is applied using an effectiveness factor model as included in the DETCHEM PBR model which also includes packed bed heat transfer correlations to transfer heat radially from the catalyst and inert sections to the tube wall. This analysis describes performance examples for the present technology. Input parameters that were common to all cases are summarized in Table 1.1. Thirteen baseline cases are described in Table 1.2a and 1.2b which do not include interspersed inert sections. Eleven cases which use interspersed inert packing with one or two inert sections are described in Tables 1.3a and 1.3b. Further, some cases include the use of an additional heat transfer aid to augment the conductivity of interspersed inert sections. Catalyst pellet thermal conductivity is increased and catalyst volumetric loading decreased in some cases. One method to achieve the increased pellet thermal conductivity is described in US2021/0245139A1 and WO 2023/129688A1. Alternatively, the catalyst section could be mixed with highly conductive particles made from SiC, industrial diamonds, or other materials of high thermal conductivity and compatible to reaction conditions of temperature, pressure, and gas composition.

TABLE 1.1

Input parameters common to all cases.

| Baseline Input | Units | Value |
| --- | --- | --- |
| Feed Mole fraction | | |
| CO2 | — | 0.2 |
| H2 | — | 0.8 |
| Catalyst parameters | | |
| pellet diameter | mm | 5 |
| tortuosity | — | 5 |
| pore diameter | micron | 1 |
| internal pellet void frac | — | 0.5 |
| Packed Bed void fraction | | 0.40 |

TABLE 1.2a

Reactor cases without stratified interspersed inert sections

| Case ID | Units | 1 | 2 | 3 | 4 | 5 | 6 |
| --- | --- | --- | --- | --- | --- | --- | --- |
| Pressure | bara | 10 | 10 | 10 | 10 | 10 | 10 |
| Feed Temperature | C. | 300 | 200 | 250 | 250 | 250 | 250 |
| Wall temperature | C. | 300 | 300 | 300 | 300 | 300 | 300 |
| Reactor internal diameter | m | 0.05 | 0.05 | 0.05 | 0.05 | 0.05 | 0.08 |
| Total Length | m | 1 | 1 | 1 | 1 | 1 | 1 |
| Reactor Volume | m3 | 1.96E−03 | 1.96E−03 | 1.96E−03 | 1.96E−03 | 1.96E−03 | 5.03E−03 |
| Catalyst length | m | 1 | 1 | 1 | 1 | 1 | 1 |
| Catalyst Volume | m3 | 1.96E−03 | 1.96E−03 | 1.96E−03 | 1.96E−03 | 1.96E−03 | 5.03E−03 |
| Superficial velocity | m/s | 0.291 | 0.241 | 0.266 | 0.266 | 0.266 | 0.266 |

TABLE 1.2a-continued

Reactor cases without stratified interspersed inert sections

| Case ID | Units | 1 | 2 | 3 | 4 | 5 | 6 |
|---|---|---|---|---|---|---|---|
| Zone 1 | | | | | | | |
| Length | m | 0.2 | 0.2 | 0.2 | 0.2 | 0.2 | 0.2 |
| Catalyst loading | kg/m3 | 1200 | 1200 | 1200 | 351 | 702 | 702 |
| pellet thermal conductivity | W/m-K | 1 | 1 | 1 | 10 | 10 | 10 |
| Zone 2 | | | | | | | |
| Length | m | 0.2 | 0.2 | 0.2 | 0.2 | 0.2 | 0.2 |
| Catalyst loading | kg/m3 | 1200 | 1200 | 1200 | 351 | 351 | 351 |
| pellet thermal conductivity | W/m-K | 1 | 1 | 1 | 10 | 10 | 10 |
| Zone 3 | | | | | | | |
| Length | m | 0.2 | 0.2 | 0.2 | 0.2 | 0.2 | 0.2 |
| Catalyst loading | kg/m3 | 1200 | 1200 | 1200 | 1200 | 1200 | 1200 |
| pellet thermal conductivity | W/m-K | 1 | 1 | 1 | 1 | 1 | 1 |
| Zone 4 | | | | | | | |
| Length | m | 0.2 | 0.2 | 0.2 | 0.2 | 0.2 | 0.2 |
| Catalyst loading | kg/m3 | 1200 | 1200 | 1200 | 1200 | 1200 | 1200 |
| pellet thermal conductivity | W/m-K | 1 | 1 | 1 | 1 | 1 | 1 |
| Zone 5 | | | | | | | |
| Length | m | 0.2 | 0.2 | 0.2 | 0.2 | 0.2 | 0.2 |
| Catalyst loading | kg/m3 | 1200 | 1200 | 1200 | 1200 | 1200 | 1200 |
| pellet thermal conductivity | W/m-K | 1 | 1 | 1 | 1 | 1 | 1 |
| Performance | | | | | | | |
| CO2 Conversion | % | 93.9 | 91.06 | 92.99 | 90.57 | 93.5 | 78.4 |
| CH4 Selectivity | % | 99.95 | 99.8 | 99.92 | 99.75 | 99.93 | 94.1 |
| Peak Temperature | C. | 714 | 707 | 708 | 680 | 682 | 700 |
| Temperature gradient (peak-wall) | C. | 414 | 407 | 408 | 380 | 382 | 400 |
| CH4 productivity | kg/d | 31.6 | 30.6 | 31.3 | 30.4 | 31.4 | 63.5 |
| Zeta-1 | C/(kg_CH4/d) | 13.1 | 13.3 | 13.1 | 12.5 | 12.2 | 6.3 |
| Zeta-2 | C × (m3_reactor * 1000)/(kg_CH4/d) | 25.7 | 26.1 | 25.6 | 24.5 | 23.9 | 31.6 |
| Zeta-3 | C × (m3_cat * 1000)/(kg_CH4/d) | 25.7 | 26.1 | 25.6 | 24.5 | 23.9 | 31.6 |

Over a range of tube diameters and inlet temperatures for 10 bara with a constant wall temperature of 300 C, a peak temperature exceeding 680 C is shown in case 4. The temperature rise within the reactor ranges from 380 C to 414 C as defined by the difference between the peak temperature and the wall temperature. The use of a highly conductive catalyst particle (as defined by a pellet thermal conductivity greater than about 2 W/m-K) helps to reduce the peak reactor bed temperature but alone is insufficient to substantially lower the reaction exotherm.

A productivity metric (zeta-1) is defined as the temperature rise defined by the peak temperature minus the wall temperature (or average wall temperature if not constant) divided by the production of methane in kg/day. For case 4, the temperature exotherm is 380 C for a productivity of 30.4 kg/day of methane for a zeta-1 value of 12.5 C/kg_CH4/day. For comparison, zeta-1 as calculated from the Shirsath data is about 700 C/kg_CH4/day. A second productivity metric (zeta-2) is defined as zeta-1 multiplied by the total reactor volume×1000. A third productivity metric (zeta-3) is defined as zeta-1 multiplied by the catalyst section volume×1000.

The more optimal reactor system for methanation will have the lowest or minimum value of zeta-1, zeta-2, and zeta-3. For the cases in Table 1.2a the value of zeta-2 and zeta-3 exceed 23 while the value of zeta-1 can be reduced to 6.3 when zeta-2 and zeta-3 exceed 30. That is the inventive stratified interspersed inert reactor as seen in Tables 1.3a and 1.3b produces more methane for a lower temperature gradient.

TABLE 1.2b

Reactor cases without stratified interspersed inert sections

| Case ID | Units | 7 | 8 | 9 | 10 | 11 | 12 | 13 |
|---|---|---|---|---|---|---|---|---|
| Pressure | bara | 10 | 10 | 10 | 2 | 2 | 2 | 10 |
| Feed Temperature | C. | 250 | 250 | 250 | 250 | 250 | 250 | 250 |
| Wall temperature | C. | 300 | 300 | 300 | 300 | 300 | 300 | 350 |

TABLE 1.2b-continued

Reactor cases without stratified interspersed inert sections

| Case ID | Units | 7 | 8 | 9 | 10 | 11 | 12 | 13 |
|---|---|---|---|---|---|---|---|---|
| Reactor internal diameter | m | 0.08 | 0.08 | 0.08 | 0.08 | 0.08 | 0.08 | 0.05 |
| Total Length | m | 1 | 1 | 1 | 1 | 1 | 1 | 1 |
| Reactor Volume | m3 | 5.03E−03 | 5.03E−03 | 5.03E−03 | 5.03E−03 | 5.03E−03 | 5.03E−03 | 1.96E−03 |
| Catalyst length | m | 1 | 1 | 1 | 1 | 1 | 1 | 1 |
| Catalyst Volume | m3 | 5.03E−03 | 5.03E−03 | 5.03E−03 | 5.03E−03 | 5.03E−03 | 5.03E−03 | 1.96E−03 |
| Superficial velocity | m/s | 0.266 | 0.532 | 0.053 | 0.266 | 0.266 | 0.266 | 0.266 |
| Zone 1 | | | | | | | | |
| Length | m | 0.2 | 0.2 | 0.2 | 0.2 | 0.2 | 0.2 | 0.2 |
| Catalyst loading | kg/m3 | 1200 | 1200 | 1200 | 1200 | 702 | 281 | 1200 |
| pellet thermal conductivity | W/m-K | 1 | 1 | 1 | 1 | 10 | 10 | 1 |
| Zone 2 | | | | | | | | |
| Length | m | 0.2 | 0.2 | 0.2 | 0.2 | 0.2 | 0.2 | 0.2 |
| Catalyst loading | kg/m3 | 1200 | 1200 | 1200 | 1200 | 351 | 421 | 1200 |
| pellet thermal conductivity | W/m-K | 1 | 1 | 1 | 1 | 10 | 10 | 1 |
| Zone 3 | | | | | | | | |
| Length | m | 0.2 | 0.2 | 0.2 | 0.2 | 0.2 | 0.2 | 0.2 |
| Catalyst loading | kg/m3 | 1200 | 1200 | 1200 | 1200 | 1200 | 1200 | 1200 |
| pellet thermal conductivity | W/m-K | 1 | 1 | 1 | 1 | 1 | 1 | 1 |
| Zone 4 | | | | | | | | |
| Length | m | 0.2 | 0.2 | 0.2 | 0.2 | 0.2 | 0.2 | 0.2 |
| Catalyst loading | kg/m3 | 1200 | 1200 | 1200 | 1200 | 1200 | 1200 | 1200 |
| pellet thermal conductivity | W/m-K | 1 | 1 | 1 | 1 | 1 | 1 | 1 |
| Zone 5 | | | | | | | | |
| Length | m | 0.2 | 0.2 | 0.2 | 0.2 | 0.2 | 0.2 | 0.2 |
| Catalyst loading | kg/m3 | 1200 | 1200 | 1200 | 1200 | 1200 | 1200 | 1200 |
| pellet thermal conductivity | W/m-K | 1 | 1 | 1 | 1 | 1 | 1 | 1 |
| Performance | | | | | | | | |
| CO2 Conversion | % | 80.5 | 75.8 | 95.4 | 89.6 | 92.5 | 91.4 | 90.96 |
| CH4 Selectivity | % | 96.2 | 89.4 | 99.97 | 99.82 | 99.95 | 99.91 | 99.78 |
| Peak Temperature | C. | 711 | 709 | 711 | 624 | 614 | 598 | 713 |
| Temperature gradient (peak-wall) | C. | 411 | 409 | 411 | 324 | 314 | 298 | 363 |
| CH4 productivity | kg/d | 66.7 | 116.7 | 16.4 | 15.4 | 15.9 | 15.7 | 30.5 |
| Zeta-1 | C/(kg_CH4/d) | 6.2 | 3.5 | 25.0 | 21.0 | 19.7 | 18.9 | 11.9 |
| Zeta-2 | C × (m3_reactor * 1000)/(kg/d) | 31.0 | 17.6 | 125.7 | 105.7 | 99.1 | 95.2 | 23.3 |
| Zeta-3 | C × (m3_cat * 1000)/(kg/d) | 31.0 | 17.6 | 125.7 | 105.7 | 99.1 | 95.2 | 23.3 |

Without the use of interspersed inert sections, the exotherm can be reduced at the expense of reactor productivity. Case 12 uses a lower inlet feed temperature, a lower catalyst loading volume in zone 1 and 2, and a higher catalyst thermal conductivity in zone 1 and 2 without interspersed inert sections. Case 12 to show a peak temperature of 598 C which is a lower temperature increase of 298 C versus results from Table 1a cases, but the reactor productivity in kg/day of methane produced has decreased. For case 12, zeta-1 is about 19. The best case without the use of interspersed inert sections is case 8 with a zeta-1 of 3.5 and values of zeta-2 and zeta-3 greater than 17. Case 8 is further disadvantaged by a lower per pass $CO_2$ conversion of about 76%. Performance is improved using stratified interspersed inert sections as shown in Table 1.3a and 1.3b.

TABLE 1.3a

Reactor cases with stratified interspersed inert section

| Case ID | Units | 14 | 15 | 16 | 17 | 18 |
|---|---|---|---|---|---|---|
| Pressure | bara | 10 | 10 | 10 | 10 | 10 |
| Feed Temperature | C. | 250 | 350 | 350 | 350 | 300 |
| Wall temperature | C. | 350 | 350 | 350 | 350 | 350 |
| Reactor internal diameter | m | 0.05 | 0.05 | 0.05 | 0.05 | 0.05 |
| Total Length | m | 1 | 1 | 1 | 1 | 1 |
| Reactor Volume | m3 | 1.96E−03 | 1.96E−03 | 1.96E−03 | 1.96E−03 | 1.96E−03 |
| Catalyst length | m | 0.90 | 0.90 | 0.90 | 0.90 | 0.90 |
| Catalyst Volume | m3 | 1.77E−03 | 1.77E−03 | 1.77E−03 | 1.77E−03 | 1.77E−03 |
| Superficial velocity | m/s | 0.266 | 0.317 | 0.317 | 0.317 | 0.291 |
| Zone 1 | | | | | | |
| Length | m | 0.1 | 0.2 | 0.1 | 0.1 | 0.1 |
| Catalyst loading | kg/m3 | 1200 | 1200 | 702 | 421 | 421 |
| pellet thermal conductivity | W/m-K | 1 | 1 | 10 | 10 | 10 |
| Zone 2 | | | | | | |
| Length | m | 0.1 | 0.1 | 0.1 | 0.1 | 0.1 |
| Catalyst loading | kg/m3 | 0 | 0 | 0 | 0 | 0 |
| pellet thermal conductivity | W/m-K | 1 | 1 | 10 | 10 | 10 |
| Zone 3 | | | | | | |
| Length | m | 0.2 | 0.2 | 0.2 | 0.2 | 0.2 |
| Catalyst loading | kg/m3 | 1200 | 1200 | 1200 | 1200 | 1200 |
| pellet thermal conductivity | W/m-K | 1 | 1 | 1 | 1 | 1 |
| Zone 4 | | | | | | |
| Length | m | 0.2 | 0.2 | 0.2 | 0.2 | 0.2 |
| Catalyst loading | kg/m3 | 1200 | 1200 | 1200 | 1200 | 1200 |
| pellet thermal conductivity | W/m-K | 1 | 1 | 1 | 1 | 1 |
| Zone 5 | | | | | | |
| Length | m | 0.4 | 0.3 | 0.4 | 0.4 | 0.4 |
| Catalyst loading | kg/m3 | 1200 | 1200 | 1200 | 1200 | 1200 |
| pellet thermal conductivity | W/m-K | 1 | 1 | 1 | 1 | 1 |
| Performance | | | | | | |
| CO2 Conversion | % | 89.4 | 91.6 | 92.5 | 92.3 | 91.6 |
| CH4 Selectivity | % | 99.61 | 99.82 | 99.88 | 99.87 | 99.83 |
| Peak Temperature | C. | 714 | 726 | 715 | 706.5 | 699.7 |
| Temperature gradient (peak-wall) | C. | 364 | 376 | 365 | 357 | 350 |
| CH4 productivity | kg/d | 30.0 | 30.8 | 31.1 | 31.0 | 30.8 |
| Zeta-1 | C/kg/d | 12.1 | 12.2 | 11.7 | 11.5 | 11.4 |
| Zeta-2 | C × (m3_reactor * 1000)/kg/d | 23.9 | 24.0 | 23.1 | 22.6 | 22.3 |
| Zeta-3 | C × (m3_cat * 1000)/(kg/d) | 21.5 | 21.6 | 20.8 | 20.3 | 20.1 |

The use of a single stratified interspersed inert section is shown in Table 1.3a. The peak temperature remains near 700 C for these cases where the wall temperature is held constant at 350 C.

TABLE 1.3b

Reactor cases with stratified interspersed inert section

| Case ID | Units | 19 | 20 | 21 | 22 | 23 | 24 |
|---|---|---|---|---|---|---|---|
| Pressure | bara | 10 | 10 | 10 | 10 | 10 | 10 |
| Feed Temperature | C. | 250 | 300 | 300 | 300 | 300 | 300 |
| Wall temperature | C. | 350 | 350 | 350 | 350 | 350 | 350 |

TABLE 1.3b-continued

Reactor cases with stratified interspersed inert section

| Case ID | Units | 19 | 20 | 21 | 22 | 23 | 24 |
|---|---|---|---|---|---|---|---|
| Reactor internal diameter | m | 0.05 | 0.08 | 0.08 | 0.08 | 0.08 | 0.08 |
| Total Length | m | 1 | 1.75 | 1.75 | 1.75 | 2.3 | 6.8 |
| Reactor Volume | m3 | 1.96E−03 | 8.80E−03 | 8.80E−03 | 8.80E−03 | 1.16E−02 | 3.42E−02 |
| Catalyst length | m | 0.90 | 0.85 | 0.85 | 0.75 | 0.80 | 5.30 |
| Catalyst Volume | m3 | 1.77E−03 | 4.27E−03 | 4.27E−03 | 3.77E−03 | 4.02E−03 | 2.66E−02 |
| Superficial velocity | m/s | 0.266 | 0.583 | 0.583 | 0.583 | 0.583 | 0.583 |
| Zone 1 | | | | | | | |
| Length | m | 0.1 | 0.2 | 0.2 | 0.2 | 0.2 | 0.2 |
| Catalyst loading | kg/m3 | 421 | 351 | 351 | 351 | 351 | 351 |
| pellet thermal conductivity | W/m-K | 10 | 10 | 10 | 10 | 10 | 10 |
| Zone 2 | | | | | | | |
| Length | m | 0.1 | 0.4 | 0.4 | 0.7 | 0.7 | 0.7 |
| Catalyst loading | kg/m3 | 0 | 0 | 0 | 0 | 0 | 0 |
| pellet thermal conductivity | W/m-K | 10 | 50 | 50 | 50 | 50 | 50 |
| Zone 3 | | | | | | | |
| Length | m | 0.2 | 0.15 | 0.15 | 0.05 | 0.1 | 0.1 |
| Catalyst loading | kg/m3 | 1200 | 105 | 105 | 105 | 105 | 105 |
| pellet thermal conductivity | W/m-K | 1 | 1 | 10 | 10 | 10 | 10 |
| Zone 4 | | | | | | | |
| Length | m | 0.2 | 0.4 | 0.4 | 0.6 | 0.8 | 0.8 |
| Catalyst loading | kg/m3 | 1200 | 0 | 0 | 0 | 0 | 0 |
| pellet thermal conductivity | W/m-K | 1 | 50 | 50 | 50 | 50 | 50 |
| Zone 5 | | | | | | | |
| Length | m | 0.4 | 0.5 | 0.5 | 0.5 | 0.5 | 5 |
| Catalyst loading | kg/m3 | 1200 | 702 | 702 | 702 | 211 | 211 |
| pellet thermal conductivity | W/m-K | 1 | 10 | 10 | 10 | 10 | 10 |
| Performance | | | | | | | |
| $CO_2$ Conversion | % | 89.1 | 82.8 | 83.2 | 81.0 | 81.6 | 93.9 |
| $CH_4$ Selectivity | % | 99.58 | 97.82 | 98 | 96.8 | 97.29 | 99.96 |
| Peak Temperature | C. | 720 | 653 | 644 | 616 | 597 | 597 |
| Temperature gradient (peak-wall) | C. | 370 | 303 | 294 | 266 | 247 | 247 |
| $CH_4$ productivity | kg/d | 29.9 | 139.7 | 140.6 | 135.2 | 136.8 | 161.6 |
| Zeta-1 | C/kg/d | 12.4 | 2.2 | 2.1 | 2.0 | 1.8 | 1.5 |
| Zeta-2 | C × (m3_reactor * 1000)/kg/d | 24.3 | 19.1 | 18.4 | 17.3 | 20.9 | 52.2 |
| Zeta-3 | C × (m3_cat * 1000)/(kg/d) | 21.9 | 9.3 | 8.9 | 7.4 | 7.3 | 40.7 |

Two interspersed inert sections between intervening catalyst sections are shown in cases 20-24 of Table 1.3b. The value of zeta-1 can be favorably reduced below 5 with a zeta-3 less than 10. The peak temperature can be reduced to less than 600 C for a wall temperature of 350 C. Increasing the length of the inert volume can reduce the peak temperature for high productivity tubular reactors as seen in case 24.

In comparison to the prior art as described by Shirsath et al 2023, whose performance leads to a small tube methane productivity of about 0.1 kg/day, the present technology will allow an industrial tube productivity exceeding 10 to 100 kg/d of methane or more. The comparison case without interspersed inert sections is seen in case 7 where about 67 kg/d of methane can be produced with a per pass conversion of about 80%. It is generally recognized that optimization on the length and number of interspersed inert sections could lead to further reduction of peak temperature, increase in production of methane in kg/day, and reduction in the performance metrics zeta-1, zeta-2, and zeta-3.

Figure 9:
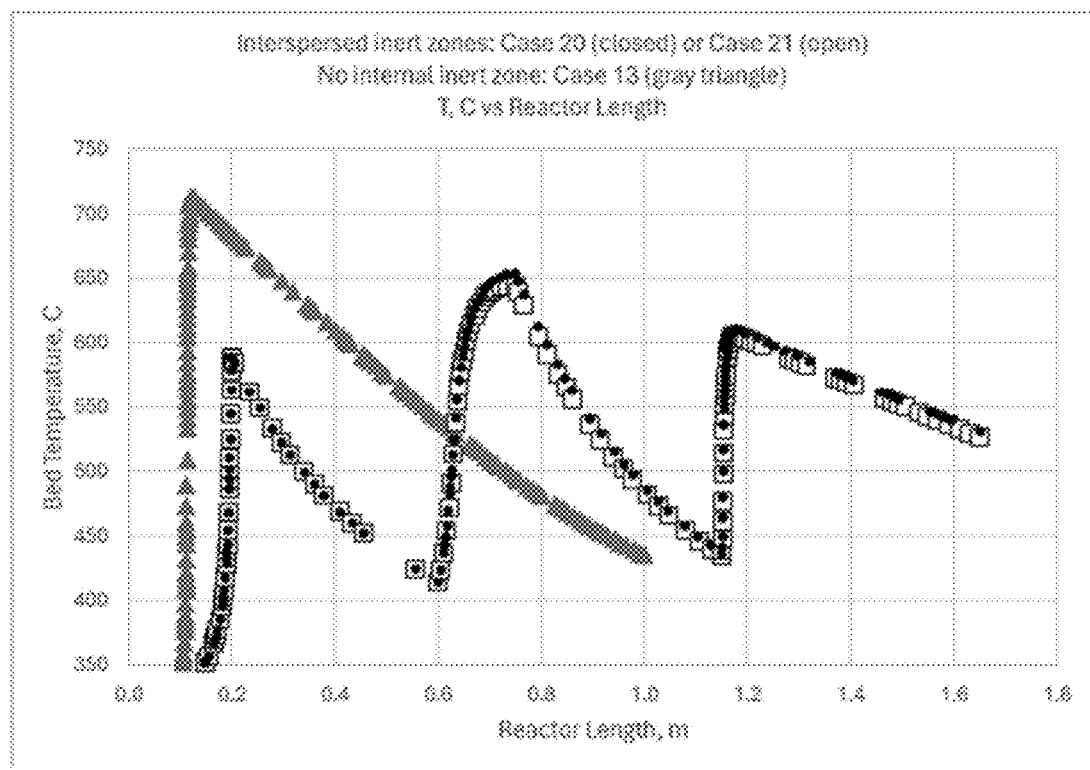
FIG. 9 is a graph that illustrates a reactor bed temperature with and without stratified internal interspersed inert sections.
Figure 10:
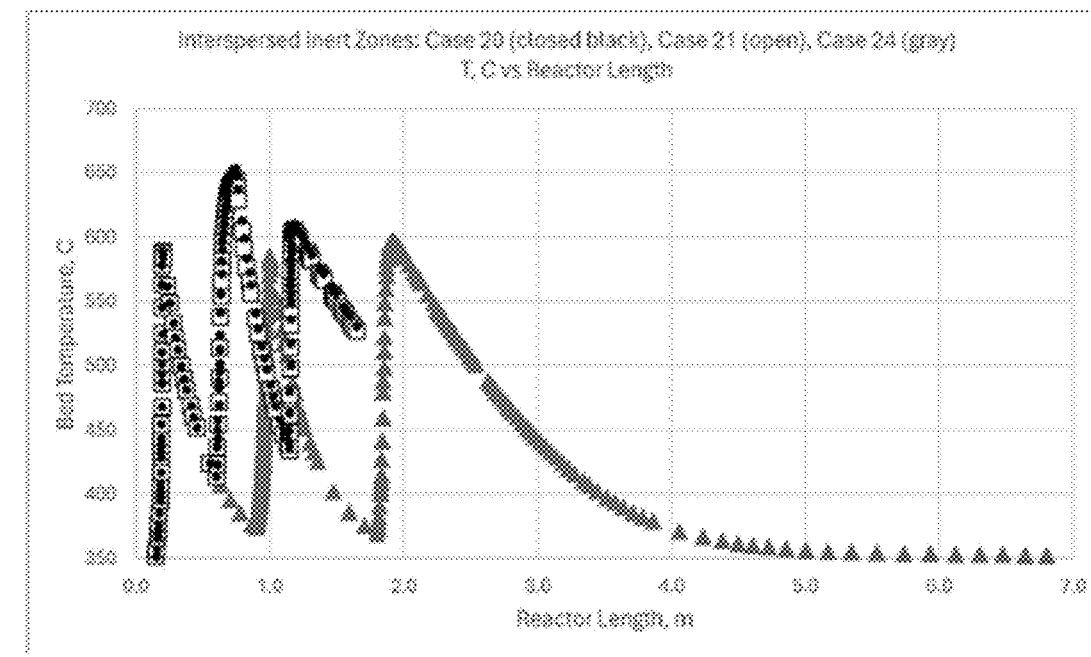
FIG. 10 is a graph that illustrates a reactor bed temperature with stratified internal interspersed inert sections for different section lengths, catalyst loading, and pellet thermal conductivity.

Comparison of reactor thermal profiles showing the impact of adding interspersed inert regions is shown in FIGS. 9 and 10. The addition of interspersed inert zones with active cooling reduces the peak temperature. Specifically, FIG. 9 is a graph that illustrates a reactor bed temperature with and without stratified internal interspersed inert sections, and FIG. 10 is a graph that illustrates a reactor bed temperature with stratified internal interspersed inert sections for different section lengths, catalyst loading, and pellet thermal conductivity.

REMARKS

The terms "example," "embodiment," and "implementation" are used interchangeably. For example, references to "one example" or "an example" in the disclosure can be, but not necessarily are, references to the same implementation; and such references mean at least one of the implementations. The appearances of the phrase "in one example" are not necessarily all referring to the same example, nor are separate or alternative examples mutually exclusive of other examples. A feature, structure, or characteristic described in connection with an example can be included in another example of the disclosure. Moreover, various features are described that can be exhibited by some examples and not by others. Similarly, various requirements are described that can be requirements for some examples but not for other examples.

The terminology used herein should be interpreted in its broadest reasonable manner, even though it is being used in conjunction with certain specific examples of the technology. The terms used in the disclosure generally have their ordinary meanings in the relevant technical art, within the context of the disclosure, and in the specific context where each term is used. A recital of alternative language or synonyms does not exclude the use of other synonyms. Special significance should not be placed upon whether or not a term is elaborated or discussed herein. The use of highlighting has no influence on the scope and meaning of a term. Further, it will be appreciated that the same thing can be said in more than one way.

Unless the context clearly requires otherwise, throughout the description and the claims, the words "comprise," "comprising," and the like are to be construed in an inclusive sense, as opposed to an exclusive or exhaustive sense—that is to say, in the sense of "including, but not limited to." As used herein, the terms "connected," "coupled," and any variants thereof mean any connection or coupling, either direct or indirect, between two or more elements; the coupling or connection between the elements can be physical, logical, or a combination thereof. Additionally, the words "herein," "above," "below," and words of similar import can refer to this application as a whole and not to any particular portions of this application. Where context permits, words in the above Detailed Description using the singular or plural number may also include the plural or singular number, respectively. The word "or" in reference to a list of two or more items covers all of the following interpretations of the word: any of the items in the list, all of the items in the list, and any combination of the items in the list. The term "module" refers broadly to software components, firmware components, and/or hardware components.

While specific examples of technology are described above for illustrative purposes, various equivalent modifications are possible within the scope of the invention, as those skilled in the relevant art will recognize. For example, while processes or blocks are presented in a given order, alternative implementations can perform routines having steps, or employ systems having blocks, in a different order, and some processes or blocks may be deleted, moved, added, subdivided, combined, and/or modified to provide alternative or sub-combinations. Each of these processes or blocks can be implemented in a variety of different ways. Also, while processes or blocks are at times shown as being performed in series, these processes or blocks can instead be performed or implemented in parallel, or can be performed at different times. Further, any specific numbers noted herein are only examples such that alternative implementations can employ differing values or ranges.

Details of the disclosed implementations can vary considerably in specific implementations while still being encompassed by the disclosed teachings. As noted above, particular terminology used when describing features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed herein, unless the above Detailed Description explicitly defines such terms. Accordingly, the actual scope of the invention encompasses not only the disclosed examples but also all equivalent ways of practicing or implementing the invention under the claims. Some alternative implementations can include additional elements to those implementations described above or include fewer elements.

Any patents and applications and other references noted above, and any that may be listed in accompanying filing papers, are incorporated herein by reference in their entireties, except for any subject matter disclaimers or disavowals, and except to the extent that the incorporated material is inconsistent with the express disclosure herein, in which case the language in this disclosure controls. Aspects of the invention can be modified to employ the systems, functions, and concepts of the various references described above to provide yet further implementations of the invention.

To reduce the number of claims, certain implementations are presented below in certain claim forms, but the applicant contemplates various aspects of an invention in other forms. For example, aspects of a claim can be recited in a means-plus-function form or in other forms, such as being embodied in a computer-readable medium. A claim intended to be interpreted as a means-plus-function claim will use the words "means for." However, the use of the term "for" in any other context is not intended to invoke a similar interpretation. The applicant reserves the right to pursue such additional claim forms either in this application or in a continuing application.

We claim:

1. A modular system configured to generate renewable fuel, the modular system comprising:
   a container including:
   an inlet configured to intake water from a source exterior to the modular system;
   an inlet configured to intake a feedstock containing carbon dioxide from a source exterior to the modular system;
   an inlet configured to receive a source of power from a source exterior to the modular system;

an outlet configured to output the renewable fuel;
the container enclosing:
an electrolysis subsystem configured to:
receive water and power from the water and power inlets to perform electrolysis to produce hydrogen and oxygen; and
a methanation reactor including:
a reaction bed having a stratified arrangement of alternating sections of catalyst material and inert material, and a reactant channel traversing at least a portion of the reaction bed,
wherein the reaction bed and the reactant channel are configured to perform an exothermic reaction using hydrogen received from the electrolysis subsystem and carbon dioxide received from the feedstock inlet,
wherein the hydrogen and carbon dioxide pass through the stratified arrangement of alternating sections of catalyst material and inert material and the reactant channel to produce the renewable fuel including a hydrocarbon-based gas or liquid, and coproducts, and
wherein the hydrogen and carbon dioxide react through the reactant channel to perform the exothermic reaction in a single-pass process;
a heat transfer medium in thermal communication with the alternating sections of catalyst material and inert material,
wherein the heat transfer medium is configured to perform active cooling of the methanation reactor to remove heat from the reaction bed; and
a heat conductive member configured to remove heat radially away from the reaction bed.

2. The modular system of claim 1 further comprising:
a treatment subsystem configured to:
receive the water from the inlet, and
process the water to produce treated water.

3. The modular system of claim 1 further comprising:
a post-processing subsystem configured to:
receive the hydrocarbon-based gas or liquid from the reactor,
perform one or more processes to convert the hydrocarbon-based gas or liquid to the renewable fuel,
wherein the one or more processes include separation of products, re-pressurization, drying, cooling, or liquification of the hydrocarbon-based gas or liquid.

4. The modular system of claim 1 further comprising:
an oxygen storage tank configured to receive the oxygen output by the electrolysis subsystem; and
another outlet configured to export the oxygen stored in the oxygen storage tank.

5. The modular system of claim 1:
wherein the methanation reactor is configured to transfer heat produced from the exothermic reaction to the electrolysis subsystem, and
wherein the electrolysis subsystem is configured to utilize the heat to perform the electrolysis.

6. The modular system of claim 1:
wherein the methanation reactor is configured to transfer the water produced at the methanation reactor to the electrolysis subsystem, and
wherein the electrolysis subsystem is configured to utilize the water for performing electrolysis.

7. The modular system of claim 1 further comprising:
a scrubber subsystem configured to:
receive biogas as the feedstock including the carbon dioxide; and
perform a scrubber process of the biogas to filter out volatile compounds and produce the carbon dioxide.

8. The modular system of claim 1 further comprising:
a direct air capture subsystem comprising a porous, solid-phase sorbent material and being configured to:
receive ambient air as the feedstock including the carbon dioxide;
perform a sorbent-based processing of the ambient air to extract the carbon dioxide; and
expel remnants through a second outlet of the container.

9. The modular system of claim 1:
wherein the catalyst material includes one or more of a transition group metal, a platinum group metal, or nickel-based catalysts, and
wherein the inert material has a thermal conductivity equal to or higher than the catalyst material.

10. The modular system of claim 1, wherein the methanation reactor comprises:
multiple reactant channels passing through the reaction bed,
wherein a total number of the multiple reactant channels depends on a desired flow rate and temperature limit of the reaction bed; and
one or more coolant channels configured to pass coolant fluid through the reaction bed to moderate the temperature of the reaction bed.

11. The modular system of claim 1, wherein the reaction bed comprises:
regularly or irregularly alternating sections of the catalyst material and the inert material,
wherein each section of the catalyst material has a boundary in common with at least one section of the inert material.

12. The modular system of claim 1, wherein the methanation reactor comprises:
an inert chamber in thermal communication with the alternating sections of catalyst material and inert material of the reaction bed,
wherein the feedstock and hydrogen are is preheated to a threshold temperature as they pass through the inert chamber prior to passing through the alternating sections of catalyst material and inert material of the reaction bed.

13. The modular system of claim 1 further configured to:
separate water vapor output from the methanation reactor;
condense the water vapor output into water; and
feed the water to the electrolysis subsystem,
wherein the electrolysis subsystem is configured to use the water to perform electrolysis.

14. A modular system comprising:
an electrolysis subsystem configured to:
receive water and power from water and power inlets to perform electrolysis to produce hydrogen and oxygen; and
a methanation reactor including:
a reaction bed having a stratified arrangement of alternating sections of catalyst material and inert material, and a reactant channel traversing at least a portion of the reaction bed,
wherein the reaction bed and the reactant channel are configured to perform an exothermic reaction using-hydrogen received from the electrolysis subsystem and carbon dioxide received from a carbon dioxide source, wherein the hydrogen and carbon dioxide pass through the stratified arrangement of alternating sections of catalyst material and inert material and the reactant channel to produce a renewable fuel including a hydrocarbon-based gas or liquid, and coproducts, and wherein the hydrogen and carbon dioxide react through the reactant channel to perform the exothermic reaction in a single-pass process;

a heat transfer medium in thermal communication with the alternating sections of catalyst material and inert material, wherein the heat transfer medium is configured to perform active cooling of the methanation reactor to remove heat from the reaction bed; and a heat conductive member configured to remove heat radially away from the reaction bed.

* * * * *